United States Patent [19]

Mazzio et al.

[11] Patent Number: 5,741,252
[45] Date of Patent: Apr. 21, 1998

[54] ADJUSTABLE CLAMP FOR BONE FIXATION ELEMENT

[75] Inventors: Michael Mazzio, Schwenksville; Beat Schenk, Paoli; Dianne Herrin, Brandamore, all of Pa.

[73] Assignee: Synthes U.S.A., Paoli, Pa.

[21] Appl. No.: 872,089

[22] Filed: Jun. 10, 1997

Related U.S. Application Data

[63] Continuation of Ser. No. 622,433, Mar. 25, 1996, abandoned.

[51] Int. Cl.$^6$ ............................................. A61B 17/62
[52] U.S. Cl. ........................................... 606/54; 606/56
[58] Field of Search ................... 606/54–59; 269/254 R, 269/254 CS

[56] References Cited

U.S. PATENT DOCUMENTS

| | | | |
|---|---|---|---|
| 1,772,885 | 8/1930 | Case | 269/38 |
| 2,371,519 | 3/1945 | Haynes . | |
| 2,406,987 | 9/1946 | Anderson . | |
| 2,687,720 | 8/1954 | Haboush . | |
| 2,932,029 | 4/1960 | De Nicolo | 269/254 R |
| 3,044,512 | 7/1962 | Jones | 269/254 R |
| 4,244,360 | 1/1981 | Dohogne . | |
| 4,258,708 | 3/1981 | Gentile . | |
| 4,273,116 | 6/1981 | Chiquet . | |
| 4,393,868 | 7/1983 | Teague . | |
| 4,483,334 | 11/1984 | Murray . | |
| 4,535,763 | 8/1985 | Jaquet . | |
| 4,662,365 | 5/1987 | Gotzen et al. . | |
| 4,745,913 | 5/1988 | Castaman et al. . | |
| 4,980,631 | 12/1990 | Hardy . | |
| 5,002,542 | 3/1991 | Frigg . | |
| 5,021,054 | 6/1991 | Monfardini et al. . | |
| 5,095,919 | 3/1992 | Monticelli et al. | 606/56 |
| 5,160,335 | 11/1992 | Wegenknecht . | |

FOREIGN PATENT DOCUMENTS

| | | |
|---|---|---|
| 0 374 093 A1 | 6/1990 | European Pat. Off. . |
| 0 509 322 A1 | 10/1992 | European Pat. Off. . |
| 0 604 697 A1 | 7/1994 | European Pat. Off. . |
| 295 12 917 U1 | 10/1995 | Germany . |
| 2 024 632 | 1/1980 | United Kingdom . |
| WO 86/02822 | 5/1986 | WIPO . |
| WO 91/11149 | 8/1991 | WIPO . |
| WO 94/28829 | 12/1994 | WIPO . |

OTHER PUBLICATIONS

Ilizarov External Fixator, Original Equipment of the Kurgan All–Union Scientific Center for Restorative Traumatology and Orthopaedics, Prof. A. Bianchi Maiocchi (1988).
Product Brochure, Torus External Fixation System, Zimmer, Inc.
Product Brochure, Wire Tension Treatment of Complex Tibial Plateau & Pilon Fractures, Ace Medical Company (1992).
Product Brochure, Fixano Ring Fixator, Fixano Z.A.
The Ilizarov External Fixatore, General Surgical Technique Brochure, Richards Medical Company (1988).
Product Brochure, Monticelli Spinelli External Fixation System, Jaquet Orthopedie S.A.

*Primary Examiner*—Michael Buiz
*Assistant Examiner*—David O. Reip
*Attorney, Agent, or Firm*—Fish & Richardson P.C.

[57] ABSTRACT

A clamp for fixing bone pins or wires to an external frame is disclosed. The clamp has a central post, an upper vise plate and a lower vise plate urged together on the post, by a spring for provisional placement, a nut for positively locking the vise plates together on a frame, and a pin clamp that can be moved along the axis of the central post, and can receive and clamp either a bone pin or a bone wire. The pin or wire has unlimited angular movement in two planes. The clamp is a captive unit that requires no intraoperative assembly.

24 Claims, 3 Drawing Sheets

ADJUSTABLE CLAMP FOR BONE FIXATION ELEMENT

This is a continuation of application Ser. No. 08/622,433, filed Mar. 25, 1996, now abandoned.

FIELD OF THE INVENTION

The invention relates generally to the field of external fixation as a means for reducing and stabilizing bone fractures. More particularly, the invention is directed toward securing a rigid external frame to pins or wires that engage bone fragments.

BACKGROUND OF THE INVENTION

One means of stabilizing and reducing severe bone fractures is through external fixation, i.e., the use of an external frame connected to pins or wires that pass through the skin and engage the bone fragments. External fixation is used where bone fragments must be post-operatively manipulated to some extent, or where disruption of surrounding tissue must be minimized.

The primary structural support for an external fixation system is provided by a rigid external frame comprising circular or rod-shaped members or combinations thereof. Each member may have a polygonal or other suitable cross-section. To this external frame are attached a plurality pins or wires that engage bone fragments on either side of the fracture. By securely fixing these wires or pins to the frame, the fracture can be stabilized during the healing process.

Bone wires and bone pins function to secure bone fragments in distinct ways. Bone pins have a diameter sufficiently large to remain essentially rigid under bending forces; for example, a diameter between 4mm and 6mm. The distal end of a bone pin typically has a self-drilling, self-tapping thread that is used to secure the pin to the bone. The proximal end of the pin is attached to the external frame.

A bone wire has a smaller diameter than a bone pin, typically between 1.5mm and 2.8mm, and depends for its rigidity on tensile loads applied through the frame during use. A bone wire is often provided with self-drilling flutes at the distal end, and is drilled completely through the bone, exiting through the skin on the opposite side of the bone. The bone wire is clamped to the external frame at one end, and then placed under tension before being clamped at the other end to another part of the frame. External frames suitable for use with bone wires often contain arcuate members surrounding or partially surrounding the bone for clamping the wire on both sides.

The term "bone fixation element" is used herein to include both bone wires and bone pins.

When clamping a bone fixation element to a frame, it is critical that all components be precisely aligned in order to avoid applying unwanted side loads. Side loads on bone fixation elements can cause bone and soft tissue damage, as well as misalignment at the fracture site. To properly compensate for misalignment between the frame and the bone fixation element, the clamp used to connect the fixation element to the frame must be adjustable in two translational and two rotational axes. If a clamp does not permit making all of these adjustments, the pins or wires must instead be drilled into the bone at precise locations and angles with respect to the frame. This is not always convenient or even possible.

In order to position a fixation element clamp longitudinally along the frame, the frame clamp jaws of current clamps are typically loosened, permitting play between the frame and the clamp while the clamp is positioned on the frame. This makes accurate positioning of the clamp on the frame difficult.

After a clamp is properly positioned on the frame, it is critical that the clamp positively lock the bone fixation element in position relative to the frame. Post-operative movement of a wire or pin can result in mishealing of the fracture or tissue damage at the pin or wire site.

It is often necessary for surgeons to utilize both wires and pins in reducing and stabilizing a fracture. Currently available clamps must be specifically selected or partially assembled before the operation in order to accommodate surgeons' selections, making the procedure rather inflexible once it is in progress. Furthermore, separate inventories of pin clamps and wire clamps must be maintained by the hospital.

SUMMARY OF THE INVENTION

In accordance with the invention there is provided a bone fixation element clamp that allows and facilitates the adjustment of all parameters of the clamp that affect the alignment of the bone fixation element to the frame. A set of bone fixation elements can thereby be clamped to a single frame member without inducing side loads, and without the necessity of precisely establishing the positions and angular alignments of the fixation elements to the bone during the drilling procedure.

In one aspect of the invention, there is provided a slotted hole for the adjustment of the distance from the fixation element to the frame member, and rotational adjustments in two perpendicular planes for unlimited angular alignment of the fixation element. All adjustments positively lock when the clamp is tightened.

In another aspect of the invention, the clamp comprises upper and lower jaws to grip the frame member. By urging the jaws closed with a spring, the clamp is maintained in true alignment on the frame member during positioning. This facilitates positioning the clamp on the frame member.

The bone fixation element clamp of the invention is further provided with two alternative clamping positions to accommodate either a bone wire or a bone pin.

DESCRIPTION OF THE DRAWINGS

The invention will be disclosed more fully in connection with the accompanying drawings in which.

DETAILED DESCRIPTION

Figure 1:
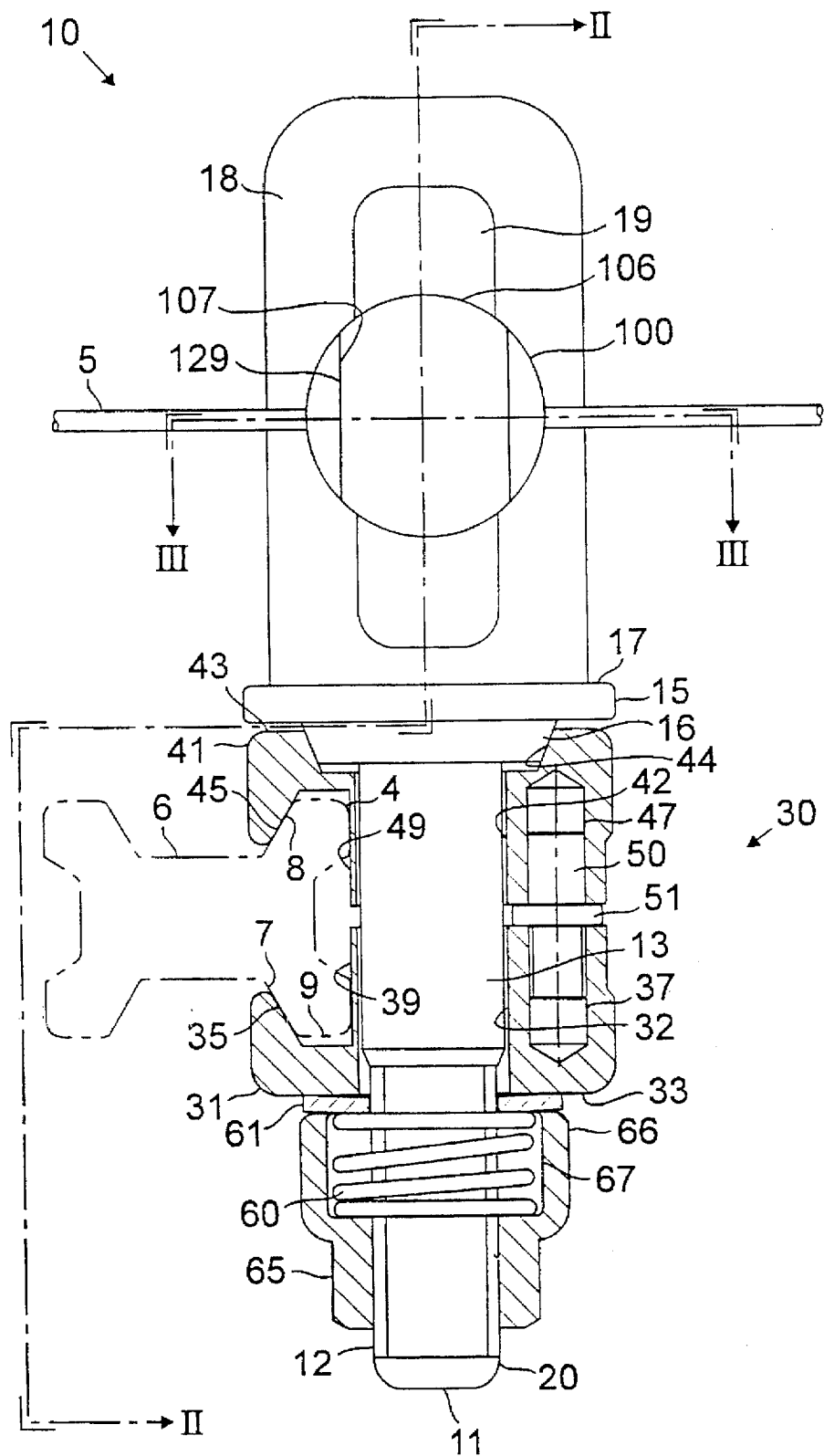
FIG. 1 is a side elevation view in partial cross section of a bone fixation element clamp according to the invention, with a bone wire clamped in position.

As shown in FIG. 1, a clamp 10 according to the invention holds a bone fixation element such as wire 5 and an external frame 6 in fixed positions relative to each other. The external frame 6 is shown in phantom with a polygonal cross section, although other frame cross sections, such as circular or elliptical, could be used in conjunction with the clamp of the invention.

Figure 2:
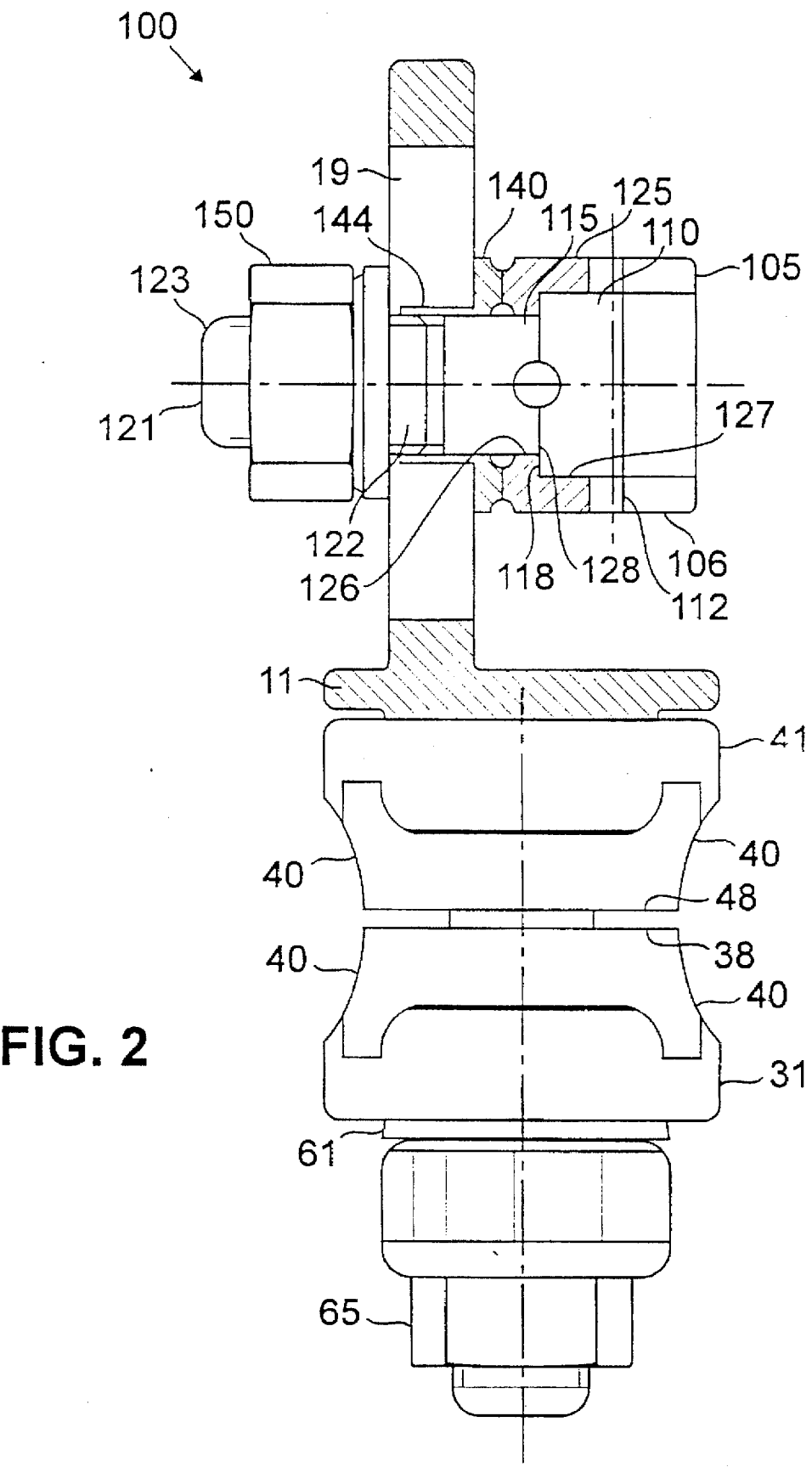
FIG. 2 is a side elevation view in partial cross section of a bone fixation element clamp of FIG. 1, taken along the line II—II.

As best illustrated in FIGS. 1 & 2, the clamp 10 of the invention comprises a post member 11, a frame clamping assembly 30, and a fixation element clamping assembly 100.

The post member 11 has a threaded end 12, a cylindrical portion 13 adjacent the threaded end 12, and a shoulder portion 15 adjacent the cylindrical portion 13. The shoulder portion 15 has a truncated conical boss 16 protruding downward toward the cylindrical portion 13. Extending perpendicularly from a top surface 17 of the shoulder portion 15 opposite the conical boss 16 is adjusting plate 18, defining a rectangular slot 19. The slot 19 extends in a direction parallel to the central axis of the post member.

The frame clamping assembly 30 of the clamp 10 is provided to grip and positively lock on the external frame 6. As shown in FIG. 1, the frame clamping assembly comprises a lower vise plate 31, an upper vise plate 41, a spring 60, a spring washer 61, and a nut 65. The components are assembled onto post member 11.

The generally cylindrical lower vise plate 31 defines a first central bore 32 that loosely fits on the cylindrical portion 13 of the post member 11.

The generally cylindrical upper vise plate 41 defines a second central bore 42 that loosely fits on the cylindrical portion 13 of the post member 11. The upper surface 43 of the upper vise plate 41 has a conical depression 44 that mates with the conical boss 16 of post member 11. As described below, the mating conical elements 44 and 16 positively lock the post member 11 to the upper vise plate 41 when the nut 65 is tightened.

Lower and upper vise plates 31, 41 have opposing jaws 35, 45 respectively, extending generally along chords of the cylindrical vise plates. The jaws 35, 45 have contours that match corresponding surfaces 7, 8 of the frame member 6. Each of the lower and upper vise plates 31, 41 preferably have finger indentations 40 (FIG. 2), to assist the surgeon in grasping the plates during installation, as described below.

A dowel 50 maintains the jaws 35, 45 in alignment. The lower and upper vise plates 31, 41 have alignment bores 37, 47, respectively, for receiving the dowel 50. The alignment bores 32, 42, and 47 are parallel to the central bores 32, 42, and preferably diametrically opposite the jaws 35, 45. At least alignment bore 37 of the lower vise plate 31 provides a loose fit on dowel 50.

Because the lower vise plate 31 has a central bore 32 and an alignment bore 37 that loosely fit the post member 11 and dowel 50, the lower vise plate 41 is permitted to pivot with respect to the upper vise plate 41, allowing some relative angular motion between jaws 35, 45. Dowel 50 has a shoulder 51 which serves as a pivot point by contacting and spacing apart the surfaces 38, 48 (FIG. 2), of the vise plates 31, 41.

A spring washer 61 is installed over the threaded end 12 of post member 11, and contacts the lower surface 33 of the lower vise plate 31. A helical compression spring 60, also installed over the threaded end 12, urges the spring washer upward against the lower vise plate 31. The spring 60 is retained on the threaded end 12 by the nut 65. The nut 65 has an annular wall 66 forming a pocket 67 that surrounds the spring 60. After the nut 65 is threaded onto the threaded end 12, the last thread 20 is deformed to prevent the nut from being removed from the post member 11. The threaded end 12 of the post member 11 is of sufficient length to allow the nut 65 to be backed away so that the lower vise plate 31 can be separated from the upper vise plate 41, compressing spring 60.

To install the clamp 10 on the external frame 6, the nut 65 is backed away until it abuts the deformed last thread 20 on the post member 11. The spring 60 is of sufficient length to maintain compressive force on the vise plates 31, 41. The surgeon grasps the clamp assembly 10 using indentations 40, and places the jaw 45 of the upper vise plate 41 over a corresponding upper clamping surface 8 of the external frame 6. By applying downward pressure on the indentations 40 on the lower vise plate 31, the surgeon then separates the upper and lower vise plates 31, 41 against spring 60, opening the jaws 35, 45. The lower vise plate 31 moves down the cylindrical portion 13 of the central post 11, compressing the spring 60. The jaws 35, 45 are maintained in alignment by dowel 50. The lower vise plate 31 is permitted to pivot slightly due to the loose fit of the central bore 32 on the post 11, further separating the jaws 35, 45.

The maximum separation of the jaws 35, 45 is sufficient to permit upward facing jaw 35 to clear the lower periphery 9 of the external frame 6. The surgeon then releases the lower vise plate 31, allowing the spring 60 to urge the upward facing jaw 35 into contact with a lower clamping surface 7 of the external frame 6. The clamp 10 is now accurately aligned by the spring 60 in an installed position on the frame 6. The clamp may thus be assembled onto the external frame at intermediate points; the clamp need not be assembled over an end of the frame, and may be used on circular frames.

With the clamp in position, the conical boss 16 is urged into contact with conical depression 44, stabilizing the post member 11 in the upper vise plate 41 by centering it and by providing a frictional resistance to its rotation. Jaws 35, 45 are urged into contact with the external frame 6, and dowel shoulder 51 is compressed between vise plate surfaces 38, 48. Because looseness is taken up by the spring 60, the clamp 10 can be precisely positioned along the frame 6, without later introducing error by tightening the nut 65.

After positioning the clamp 10 on the external frame 6, the surgeon locks the clamp in place by tightening the nut 65 with a wrench (not shown) until the annular wall 66 of the nut contacts and compresses the spring washer 61. Forcible contact between the conical surfaces 16 and 44 positively locks the post member 11 against rotation. A camming force between the jaws 35, 45 and surfaces 7, 8 on the external frame 6 urges the outside edge 4 of the frame 6 against the inner jaw surfaces 39, 49, positively locking against translation of the clamp 10 on the frame 6.

As best shown in FIG. 2, the bone fixation element clamping assembly 100 comprises a T-shaped post 105, a cup-shaped clamping member 125, a washer 140, and an integral washer/nut 150.

Figure 3:
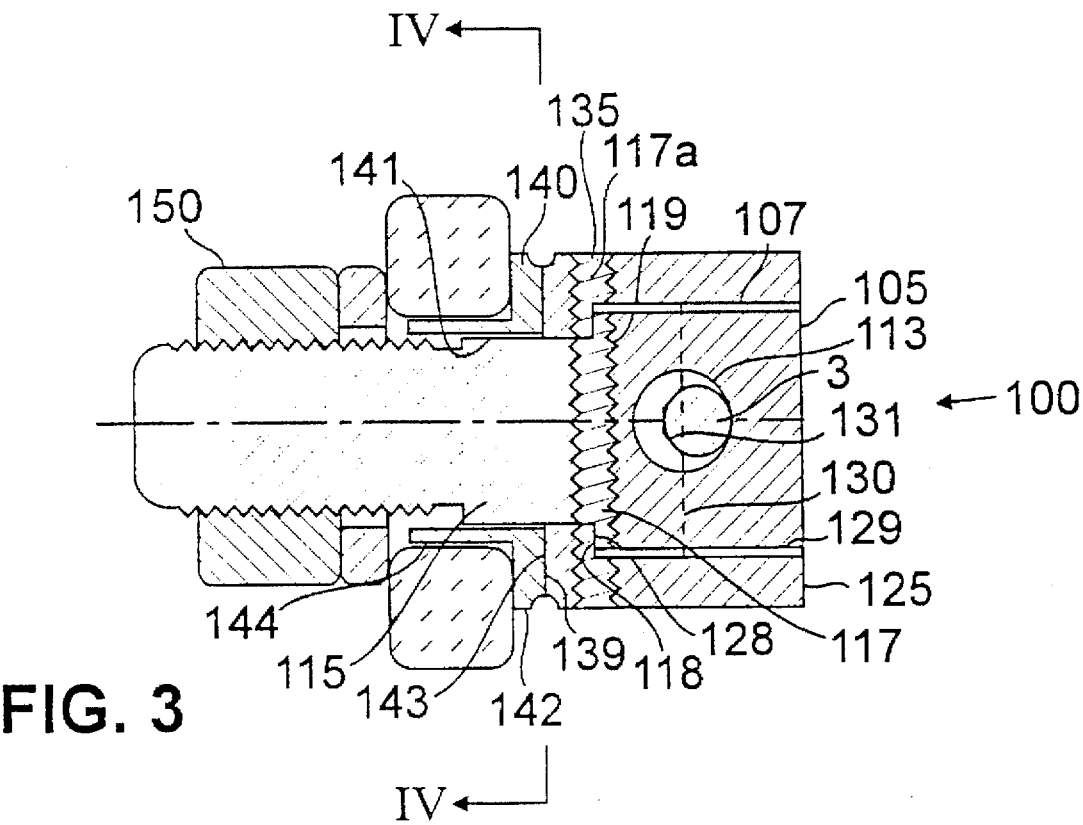
FIG. 3 is a sectional view of the bone fixation element clamp of FIG. 1, taken along the line III—III, with a bone pin clamped in position.

The post 105 has a disc-shaped head 106 with flats 107 (FIG. 1), a first cylindrical portion 110, a second cylindrical portion 115, and a threaded lower end 122. Between the head 106 and the first cylindrical portion 110 is a first shoulder 112; between the first and second cylindrical portions 110, 115 is a second shoulder 118. As shown in FIG. 3, the post 105 has a large transverse hole 113 for clamping a bone pin 3, parallel to the flats 107 and centered slightly below the first shoulder 112 (FIG. 2). Centered on the second shoulder 118 is a small transverse hole 119 for clamping a wire, perpendicular to the large transverse hole 113. The small transverse hole 119 may have internal ridges such as threads 117 for an increased tensile grip.

Returning to FIG. 2, the cup-shaped clamping member 125 has an axial hole 126 for slidingly receiving the second cylindrical portion 115 of the post 105. A bore 127 of the clamping member 125 terminates at a shoulder 128, and has a diameter for slidingly receiving the first cylindrical portion 110 of the post 105. As best seen in FIGS. 1 & 3, a slot 129 of the clamping member 125 has a width to slidingly receive the flats 107 of the post 105.

As shown in FIG. 3, the base 130 of the slot 129 has a V-groove 131 aligned with the large transverse hole 113 in the post 105. When a bone pin 3 is clamped in the bone fixation element clamping assembly 100, it is compressed between the V-groove 131 and an opposing portion of the large transverse hole 113.

Centered slightly above the shoulder 128 of the clamping member 125 is a small transverse hole 135. The small transverse hole 135 is perpendicular to the V-groove 131, and aligned with the small transverse hole 119 in the post 105. The small transverse hole 135 may have internal ridges such as threads 117a for increased tensile grip. A bone wire is clamped in the bone fixation element clamping assembly 100 by compressing it between opposing portions of the small transverse holes 119 and 135.

Figure 4:
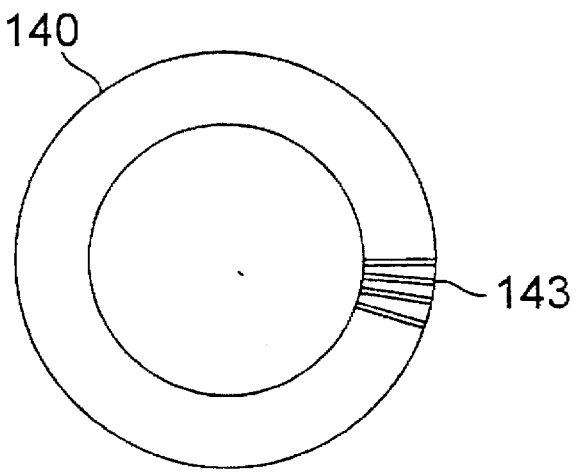
FIG. 4 is a partial sectional view of the bone fixation element clamp of FIG. 3, taken along the line IV—IV.

The washer 140 has a central hole 141 (FIG. 3) for slidably receiving the second cylindrical portion 115 of the T-shaped post 105. In a preferred embodiment, disc-shaped portion 142 of the washer 140 has a "star-grind" pattern 143 (FIG. 4), for mating with a similar pattern 139 on the clamping member 125. The "star grind" pattern mating surfaces 139, 143 provide positive rotational seating between the washer 140 and the clamping member 125.

The washer 140 further has a square boss 144 (FIG. 2) for slidingly engaging the rectangular slot 19 of the post member 11. The square boss prevents rotation of the washer 140 in the slot 19. The washer 140 can be moved in the slot 19 in order to adjust the position of the fixation element clamping assembly parallel to the axis of the post member 11. The "star-grind" pattern 139, 143, in combination with the square boss 144, permits the surgeon to apply torque to the nut/washer 150 with one hand without rotating the T-shaped post 105.

After assembling the T-shaped post 105 through the clamp member 125 and the washer 140, and inserting the square boss 144 of the washer 140 into the rectangular slot 19, an integral nut/washer 150 is threaded onto the threaded end 121 of the post 105. The last thread 123 of the post is then deformed to retain the nut/washer 150, making the fixation element clamping assembly 100 a captive assembly. By tightening the nut/washer 150, a surgeon can in one step positively lock the fixation element clamping assembly 100 in position along the rectangular slot 19, rotationally lock the clamping assembly 100 through the star grind faces 139, 143, and securely clamp either a wire or a pin.

The components comprising the clamp of the invention are fabricated from titanium, stainless steel, or another sufficiently strong material that is inert to body fluids. In a preferred embodiment, the frame clamping assembly 30 and central post 11 are titanium alloy, while the fixation element clamping assembly 100 is stainless steel.

From a consideration of the foregoing description it will be evident that a clamp 10 according to the invention permits precise clamping alignment to a bone fixation element in two rotation axes and two translation axes. Before tightening the nut 65, the central post member 11 can be rotated with respect to the vise plates 31, 41, and the frame clamping assembly 30 can be translated along the external frame 6. Before tightening the nut/washer 150, the T-shaped post 105 and cup-shaped clamping member 125 can be rotated with respect to the washer 140, and the washer 140 can be translated within the rectangular slot 19. Thus the surgeon is able to align the clamp to suit a specific relationship of the frame to the wire or pin, and securely clamp the wire or pin without introducing side loads.

I claim:

1. A clamp for attaching a bone fixation element to an external frame, comprising:

a post member;

a fixation element clamp assembly attached to said post member and having a longitudinal axis, the clamp assembly further comprising a plurality of non-parallel holes for receiving a bone fixation element, said holes extending through the clamp assembly in a non-parallel direction to said longitudinal axis;

opposing upper and lower vise plates for gripping the external frame, said vise plates having bores for receiving said post member;

retaining means on said post member for retaining said upper and lower vise plates; and compression means for urging said vise plates together.

2. The clamp of claim 1, wherein said compression means comprises a compression spring disposed between said retaining means and said vise plates.

3. The clamp of claim 1, wherein a portion of said post member is threaded and said retaining means comprises a nut mounted on said threaded portion.

4. A clamp for attaching a bone fixation element to an external frame, comprising:

a post member having a threaded portion;

a fixation element clamp assembly attached to said post member;

opposing upper and lower vise plates for gripping the external frame, said vise plates having bores for receiving said post member;

retaining means on said post member for retaining said upper and lower vise plates, said retaining means comprising a nut mounted on said threaded portion; and a spring disposed within an upward-facing annular channel on said nut for urging said vise plates together.

5. A clamp for attaching a bone fixation element to an external frame, comprising:

a post member;

a bone fixation element clamp disposed at an upper end of said post member;

opposing upper and lower vise plates disposed on said post member, for gripping the external frame;

an upward facing conical recess on an upper surface of said upper vise plate;

a downward facing conical shoulder on said post member, said conical shoulder seated in said conical recess of said upper vise plate;

compression means for urging said upper and lower vise plates onto the external frame, and said conical shoulder into said conical recess.

6. The clamp of claim 5, wherein said compression means is a spring.

7. The clamp of claim 6, further comprising a nut disposed on a lower end of said post member, said spring being compressed between said nut and said lower vise plate.

8. The clamp of claim 7, further comprising a means to retain said nut on said post member.

9. The clamp of claim 5, wherein said upper and lower vise plates have opposing recesses, said clamp further comprising a guide means seated in said recesses to restrict relative rotation of said upper and lower vise plates about said post member.

10. The clamp of claim 9, wherein said guide means comprises a dowel.

11. A clamp for attaching bone fixation elements to an external frame, comprising:
 a frame clamping assembly having an adjustment plate with an elongated slot;
 a bone fixation element clamp assembly slidably disposed in said elongated slot of said adjustment plate, said bone fixation element clamp assembly comprising
  a T-shaped central shaft having a threaded end and a head with flats, said shaft disposed within said elongated slot;
  a cup-shaped clamping member having a central bore for receiving said central shaft, and a transverse slot for receiving said flats of said shaft head;
  a nut threaded onto said threaded end of said central shaft;
  said central shaft having a first transverse hole therethrough, whereby a bone fixation element inserted in said first transverse hole is clamped in said first transverse hole by said clamping member when said nut is tightened.

12. The clamp of claim 11, wherein said central post has a second transverse hole, and said clamping member has a transverse hole aligned with the second transverse hole of said central post, whereby a bone fixation element inserted in said second transverse hole of said central post and said transverse hole of said clamping member is clamped when said nut is tightened.

13. The clamp of claim 12, wherein said second transverse hole of said central post and said transverse hole of said clamping member have internal ridges for gripping a bone wire.

14. The clamp of claim 11, further comprising means for preventing rotation of said cup-shaped clamping member as said nut is tightened.

15. The clamp of claim 14, wherein said means for preventing rotation comprises a washer disposed on said central shaft between said cup-shaped clamping member and said adjustment plate, said washer having a rectangular boss slidably disposed within said elongated slot, said cup-shaped clamping member and said washer having mating surfaces with interlocking star-grind patterns.

16. The clamp of claim 11, wherein the last thread of said threaded end of said central shaft is deformed to retain said nut.

17. The clamp of claim 11, wherein said nut has an integral washer.

18. An apparatus for attaching a bone fixation element to an external frame, comprising:
 a first post member having an adjustment plate extending from an upper shoulder, said adjustment plate having an elongated slot;
 opposing upper and lower vise plates for slidably gripping the external frame, said plates being rotatably disposed on said first post member, said plates being sufficiently separable to permit assembly onto the external frame at an intermediate point;
 a bone fixation element clamp comprising a second post member, said second post member being non-parallel to said first post member and slidably and rotatably disposed in said elongated slot;
 whereby said clamp can be rotated about said first and said second post members, and can be translated by sliding said vise plates along the external frame member and by sliding said second post member in said elongated slot.

19. The apparatus of claim 18, further comprising a compression means for urging said upper and lower vise plates together.

20. The apparatus of claim 18, further comprising a first locking means for locking said vise plates on the external frame, and a second locking means for locking said clamp on the bone fixation element.

21. The apparatus of claim 20, wherein said first post member has a threaded end, and said first locking means comprises a first nut threaded onto said threaded end of said first post member, and further wherein said second post member has a threaded end, and said second locking means comprises a second nut threaded onto said threaded end of said second post member.

22. A clamp for attaching a bone fixation element with a longitudinal axis to an external frame, comprising:
 a frame clamping assembly having opposing laws for clamping the external frame;
 a fixation element clamping assembly depending from said frame clamming assembly; and
 a spring urging said opposing jaws of said frame clamping assembly to a clamping position on the frame,
 wherein said frame clamp assembly permits rotation of the bone fixation element about a first axis other than said longitudinal axis, and said fixation element clamping assembly permits rotation of the bone fixation element about a second axis other than said first axis and said longitudinal axis.

23. The clamp of claim 22, wherein said second axis is perpendicular to said first axis.

24. The clamp of claim 23 wherein a distance from the fixation element clamping assembly to the external frame is adjustable.

* * * * *

UNITED STATES PATENT AND TRADEMARK OFFICE
CERTIFICATE OF CORRECTION

PATENT NO. : 5,741,252
DATED : April 21, 1998
INVENTOR(S) : Michael Mazzio, Beat Schenk & Dianne Herrin It is certified that error appears in the above-identified patent and that said Letters Patent is hereby corrected as shown below:

In the Claims:

Claim 22, Col. 8, line 34, delete "laws" and insert --jaws--.

Claim 22, Col. 8, line 37, delete "clamming" and insert --clamping--.

Signed and Sealed this

Seventeenth Day of August, 1999

Attest:

Q. TODD DICKINSON

Attesting Officer     Acting Commissioner of Patents and Trademarks

Disclaimer

5,741,252—Michael Mazzio, Schwenksville; Beat Schenk, Paoli; Dianne Herrin, Brandamore, all of Pa. ADJUSTABLE CLAMP FOR BONE FIXATION ELEMENT. Patent dated April 21, 1998. Disclaimer filed September 25, 2003, by the assignee, Synthes (USA).

Hereby enters this disclaimer to all claims, of said patent.

*(Official Gazette, March 2, 2004)*